(12) United States Patent  
Spork et al.

(10) Patent No.: US 6,689,318 B1  
(45) Date of Patent: Feb. 10, 2004

(54) APPARATUS FOR ANALYSIS OF PHYSIOLOGICAL FLUIDS

(75) Inventors: Allan Spork, Lyngby (DK); Bent Pedersen, Virum (DK); Niels Fremming, Herlev (DK); Kristian Jacob Hvidtfeldt, Virum (DK)

(73) Assignee: Radiometer Medical A/S, Bronshoj (DK)

( * ) Notice: Subject to any disclaimer, the term of this patent is extended or adjusted under 35 U.S.C. 154(b) by 451 days.

(21) Appl. No.: 08/776,303

(22) Filed: Feb. 24, 1997

Related U.S. Application Data

(63) Continuation of application No. PCT/DK96/00362, filed on Aug. 29, 1996.

(30) Foreign Application Priority Data

Aug. 30, 1995 (DK) ................................................ 0964/95

(51) Int. Cl.[7] .............................................. G01N 35/00
(52) U.S. Cl. ........................ 422/63; 422/100; 422/102; 436/54; 436/180
(58) Field of Search .............................. 422/63, 64, 65, 422/81, 100, 102, 104, 68.1; 436/43, 47, 48, 49, 54, 174, 180, 68, 74, 79, 66, 67; 73/864.24, 864.25

(56) References Cited

U.S. PATENT DOCUMENTS

| | | | |
|---|---|---|---|
| 3,676,076 A | * | 7/1972 | Grady ........................ 422/100 |
| 4,475,411 A | * | 10/1984 | Wellerfors ................ 73/864.24 |
| 4,478,095 A | * | 10/1984 | Bradley et al. .......... 73/864.21 |
| 4,609,017 A | * | 9/1986 | Coulter et al. ................. 141/1 |
| 4,713,974 A | * | 12/1987 | Stone ....................... 73/864.23 |
| 4,721,137 A | * | 1/1988 | Muller ......................... 141/65 |
| 4,876,926 A | * | 10/1989 | Muszak ........................ 81/3.2 |
| 4,906,433 A | * | 3/1990 | Minekane ..................... 422/64 |
| 4,919,887 A | | 4/1990 | Wakatake |
| 4,982,553 A | | 1/1991 | Itoh |
| 5,112,454 A | | 5/1992 | Tanaka et al. |
| 5,201,232 A | * | 4/1993 | Uffenheimer ............ 73/864.23 |
| 5,209,903 A | * | 5/1993 | Kanamori et al. ............ 422/65 |
| 5,230,427 A | | 7/1993 | Betts et al. |
| 5,255,574 A | * | 10/1993 | Wuerschum .................. 81/3.2 |
| 5,489,321 A | | 2/1996 | Tracey et al. |
| 5,550,053 A | * | 8/1996 | Salpeter .......................... 436/8 |
| 5,551,828 A | * | 9/1996 | Iles ............................. 414/757 |
| 5,976,468 A | * | 11/1999 | Godec et al. ............... 422/100 |

FOREIGN PATENT DOCUMENTS

| | | | |
|---|---|---|---|
| EP | 0452892 | * | 10/1991 |
| GB | 2 051 371 A | | 1/1981 |
| WO | WO91/00520 | | 1/1991 |

* cited by examiner

*Primary Examiner*—Jeffrey Snay  
(74) *Attorney, Agent, or Firm*—Bryan Cave LLP; Maurice B. Stiefel

(57) ABSTRACT

The apparatus for analysis of physiological fluids of the invention contains equipment for automatic introduction of reference fluids to a sample aggregate inlet of the apparatus. The apparatus also contains equipment for analyzing the samples.

21 Claims, 11 Drawing Sheets

Figure 1:
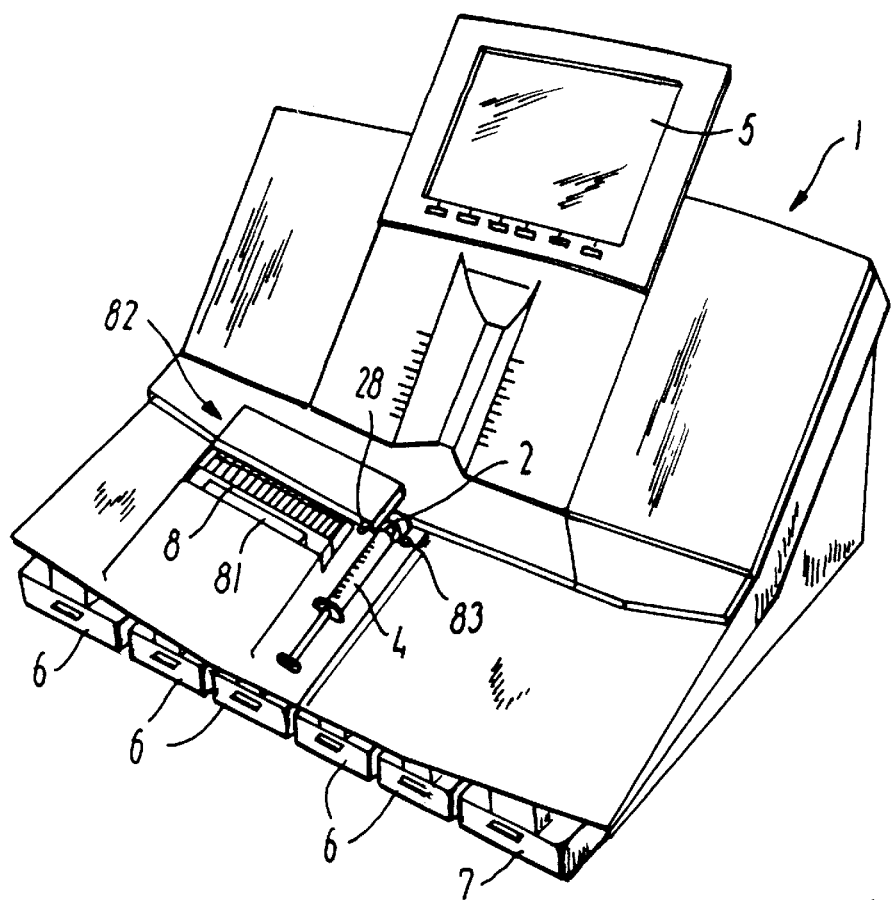

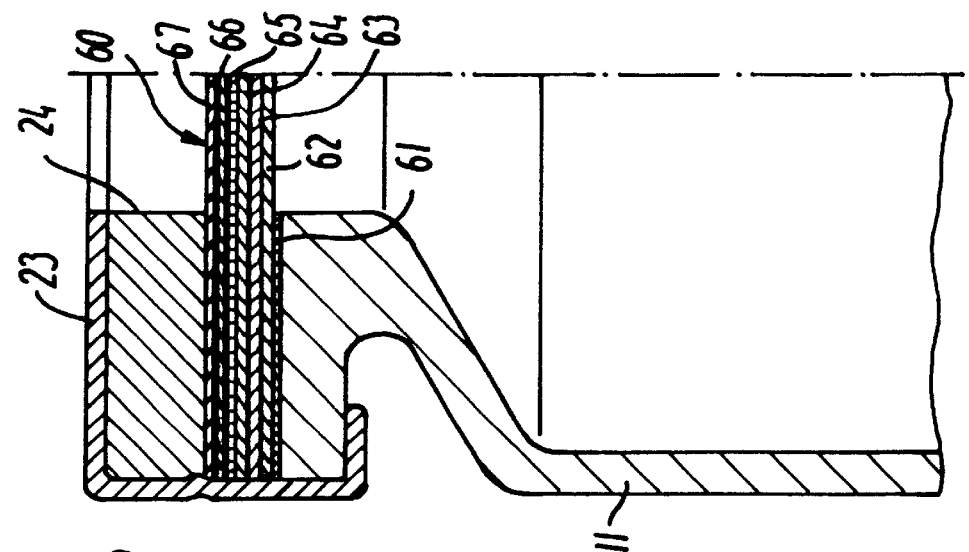
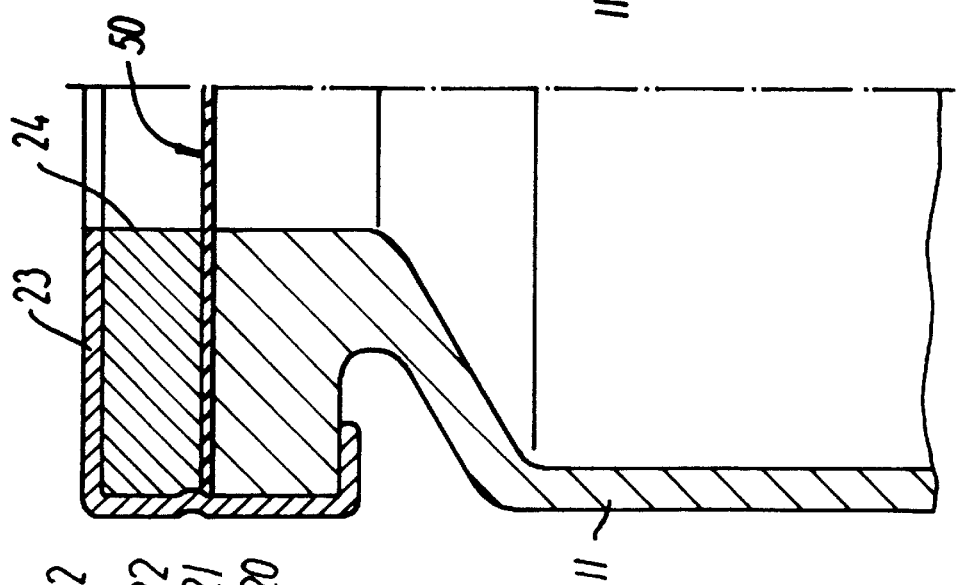
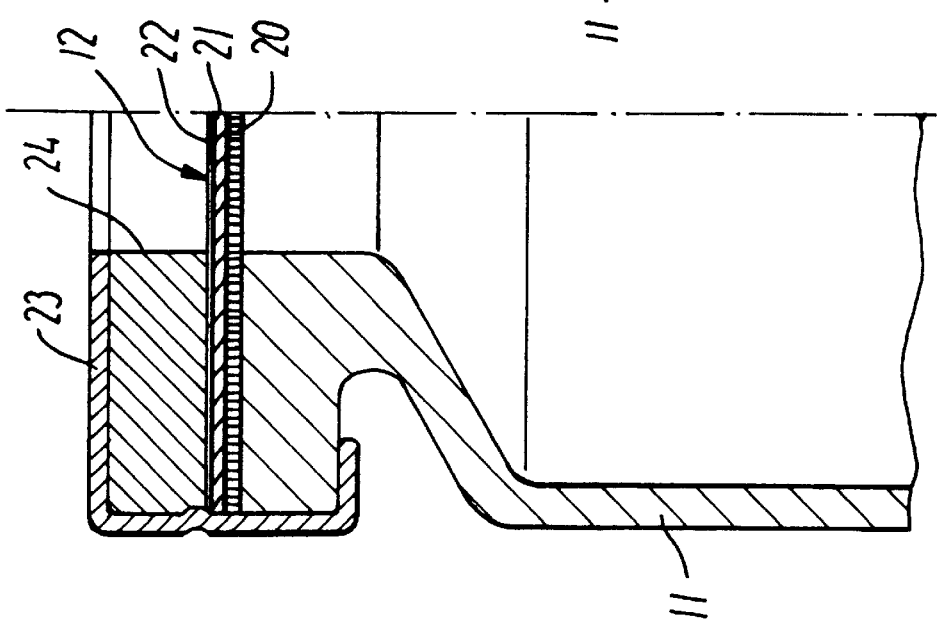

APPARATUS FOR ANALYSIS OF PHYSIOLOGICAL FLUIDS

This is a continuation of International Application PCT/DK96/00362, filed Aug. 29, 1996.

The present invention relates to automatical introduction of reference fluid in apparatus for analysis of physiological fluids.

A known apparatus of this type is an apparatus for blood gas analysis. Such apparatus are by way of example used in hospitals and medical laboratories where they are permanently ready for operation with a view to analysis of blood samples immediately after their being taken. The apparatus analyses the blood samples for example by measuring partial pressure of $CO_2$ ($pCO_2$), partial pressure of $O_2$ ($pO_2$) and pH. In order that an apparatus works in a reliable way, i.e. provides reliable measuring results, it must normally be calibrated at appropriate intervals. Furthermore, the calibration must be controlled frequently. Therefore, a quality control procedure is, among other, performed where the apparatus analyses a control solution with known values for at least some of the parameters which the apparatus is adapted to measure. According to guidelines from National Committee for Clinical Laboratory Standards (NCCLS DOCUMENT C27-A, Vol. 13, No. 6) for collection and handling an arterial specimen for pH and blood gas analysis and for calibrating the analyzer together with recommendations for an acceptable quality control program, it is recommended to perform said quality control program once per shift (i.e. three times a day by treble shift) such that three different levels (high, middle and low) for the parameters to be controlled are measured in three consecutive shifts.

So far this quality control has been performed manually in the way that an operator injects or introduces a control solution with specific contents in the analysis apparatus according to a fixed schedule, and the apparatus then carries out a control program. The result of this control is printed and if the measured values of the parameters in question lie within predetermined limits, the control is accepted, and the apparatus may be used. Otherwise it may be necessary to calibrate the apparatus before it is used for analysis of a sample. The control program is terminated by a rinse program by which the apparatus rinses itself of control solution.

The control solution is usually supplied in small containers or ampoules, the contents of one ampoule being used for one quality control. The ampoules are usually designed as ampoules with a breakable neck. Larger containers for several controls are also known. The containers for control solutions are described in the literature since the beginning of the 1970s. One of the latest publications on containers with control solutions is U.S. Pat. No. 5,230,427.

The ampoule contains both a liquid phase and a gas phase, a temperature dependent balance being between dissolved gas in the liquid phase and gas in the gas phase. In order to know the exact contents of a given gas in the solution, it is therefore necessary that the temperature of the solution in the ampoule is known, and that this temperature is uniform within the entire volume of the ampoule. In order to ensure a uniform temperature distribution, the ampoule is shaked prior to the quality control. Alternatively, it may be ensured that the ampoule has been kept at a constant known temperature for some time.

A problem with the prior art technology of manual quality control is that in the nature of the case, it requires qualified personnel efforts as there are some (human) error possibilities, for instance that a quality control is forgotten or that the quality control procedure is carried through incorrectly.

It is the object of the invention to avoid or reduce the drawbacks of the prior art.

According to the invention, an apparatus for analysis of physiological fluids, such as an apparatus for blood gas analysis, is characterized by equipment for automatic introduction of reference fluid for the apparatus, which equipment comprises a holder for concurrent hold of several sealed containers with reference fluid, means for bringing a selected container and means for opening the container into a specific position in relation to each other, means for bringing the opened container and an inlet aggregate for introduction of fluid from the container into the apparatus into a specific position in relation to each other, means for activating the inlet aggregate, means for removing the container and the inlet aggregate from each other, and programmable control means for control of the introduction of reference fluid into the apparatus.

The holder may be a detachable or non-detachable part of the apparatus. Further, the holder may comprise a device into which the sealed containers may be loaded individually or it may comprise a support means adapted for removably holding or being attached to a magazine wherein several sealed containers are concurrently held.

The control means of the device then ensures the introduction of reference fluid at pre-programmed times, the control means selecting a container with a specific reference fluid and the device then automatically ensures that the container is opened, its contents introduced into the apparatus and the container and the inlet aggregate removed from each other.

In a preferred embodiment, the inlet aggregate is constituted by the inlet aggregate of the apparatus for fluid samples for analysis. Thereby is avoided a separate aggregate for transmission of the fluid from the container to the inlet aggregate of the apparatus for fluid samples to be analysed, such as blood samples.

The apparatus according to the invention may be designed in a particularly simple way if the means for bringing a selected container and the inlet aggregate into a specific position in relation each other comprise means for moving a magazine and/or the holder of the sealed containers. The means for moving the magazine and/or the holder may further be adapted to agitate the containers such that a shaking effect is obtained.

The means for bringing a selected container and the means for opening the container into a specific position in relation to each other and the means for bringing the opened container and an inlet aggregate for introduction of fluid from the container into the apparatus into a specific position in relation to each other may be constituted by the same means. Furthermore, said positions of the container in relation to means for opening the container and in relation to an inlet aggregate for introduction of fluid from the container into the apparatus may be one and the same position.

Preferably, the means for opening the container comprise an element which is made to press against an opening area on the container which is thus opened.

In all aspects of the invention, the sealed containers with reference fluid may or may not contain both a liquid phase and a gas phase, two phases being preferred.

According to the invention, there is further provided a unit to be mounted into and to be a part of an apparatus for analysis of physiological fluids, which unit is characterized in a holder for concurrent hold of several sealed containers with reference fluid, means for bringing a selected container and means for opening the container into a specific position in relation to each other, means for bringing the opened container and an inlet aggregate for introduction of fluid from the container into the apparatus into a specific position in relation to each other, and means for removing the container and the inlet aggregate from each other. When mounted, this unit forms an integrated part of an apparatus according to the invention as described above.

According to the invention, there is further provided an ampoule containing a reference fluid and comprising a body with an opening area having an opening the circumferential edge of which lies in one and the same plane, said body being hermetically sealed by a membrane mounted to the circumferential opening edge of the body, said ampoule being characteristic in that the membrane is planar and comprises a layer of a glass material. The membrane may consist of one or several layers of glass or the membrane may comprise at least one layer of glass and at least one layer of a polymeric material. The glass material is preferably a borosilicate glass or a silicon or aluminum oxide. However, other types of glasses may be useful as well.

In the sealed ampoule the membrane may show some distortion from planar as a result of the sealing process. However, the membrane must be planar prior to the sealing process. When referring to the circumferential edge as lying in one and the same plane it has to be understood that sectional views of the circumferential edge may show any suitable linear or non-linear shape.

This ampoule may be manufactured reproducibly with a very thin (30–150 $\mu$m) and thus easily breakable membrane. Furthermore, the membrane provides the ampoule with an opening area which has a uniform thickness. Thus, the ampoule according to the invention is advantageous as compared to the well-known glass ampoules with breakable necks, these ampoules having a wall thickness of 0.5–1 mm. It has been attempted to manufacture these prior art ampoules with thin bottoms in order to use the bottom as an opening area to be broken immediately before the withdrawal of reference fluid from the ampoules. However, is has shown very difficult to produce the prior art ampoules with a uniform and reproducible thickness of the bottom. Further, these prior art ampoules turned out not to be sturdy, but did often break during transportation.

The ampoule according to the invention is also advantageous as compared to the ampoules disclosed in the above mentioned U.S. Pat. No. 5,230,427. The ampoules disclosed therein comprises a body with an opening sealed by a membrane of a polymeric layer and a metal layer. These prior art ampoules suffer from the drawback that the metal layer is exposed to corrosion and that any oxygen contained in the reference fluid may diffuse through the polymeric layer into the metal layer, thereby causing corrosion. An embodiment of these prior art ampoules are commercially available under the trade name StatPal®II, Calibration Kit, from PPG Industries, Inc., La Jolla, Calif., USA. These ampoules suffer from the drawback that they have to be kept individually in bags with a controlled atmosphere in order to maintain the composition of the reference fluid as required during storage.

Further according to the invention, there is provided another ampoule containing reference fluid and comprising a body with an opening area having an opening sealed with a membrane, which ampoule is characterized in that the opening area comprises a cap which has a penetration part provided with a through hole, which penetration part is arranged for breaking through the membrane in order to open the ampoule by movements against the body. The body is preferably oblong and the opening area is preferably placed in one end of the body. Such an ampoule is particularly suitable for use in connection with an apparatus according to the invention, thus permitting to lead a pipe through the hollow penetration part and down into the container in order to aspirate fluid for the apparatus. This tube is preferably a part of the inlet aggregate.

According to the invention, there is further provided a magazine comprising several ampoules with reference fluid for an apparatus for analysis of physiological fluids, such as an apparatus for blood gas analysis, reference fluid with predetermined content being provided in different ampoules, which magazine is arranged for loading as a unit to an apparatus of said type. Different ampoules may have different predetermined contents and the reference fluid in the ampoules may be a control solution for quality control of the apparatus. By such a magazine, the operation of an apparatus according to invention is particularly simple as the concurrent hold of several sealed containers with reference fluid by the holder, may be achieved merely by loading or attaching a new magazine.

Figure 2:
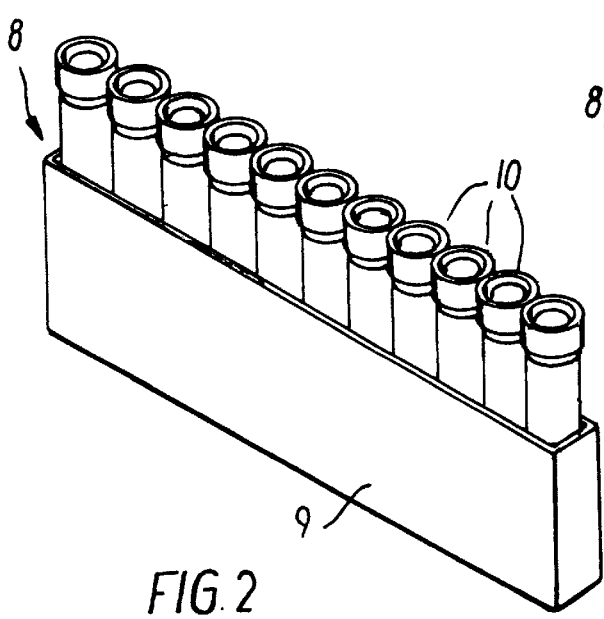
Figure 3:
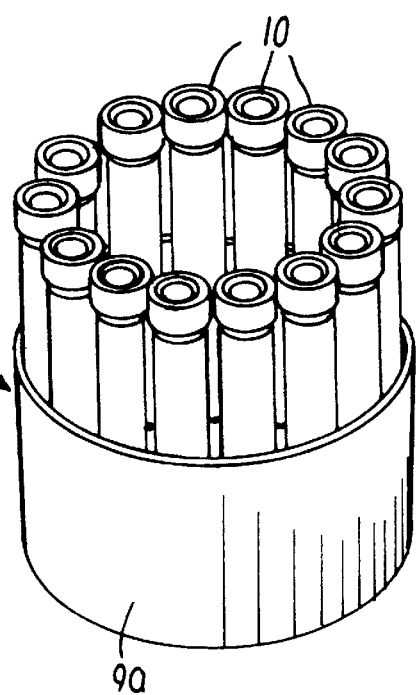
Figure 4:
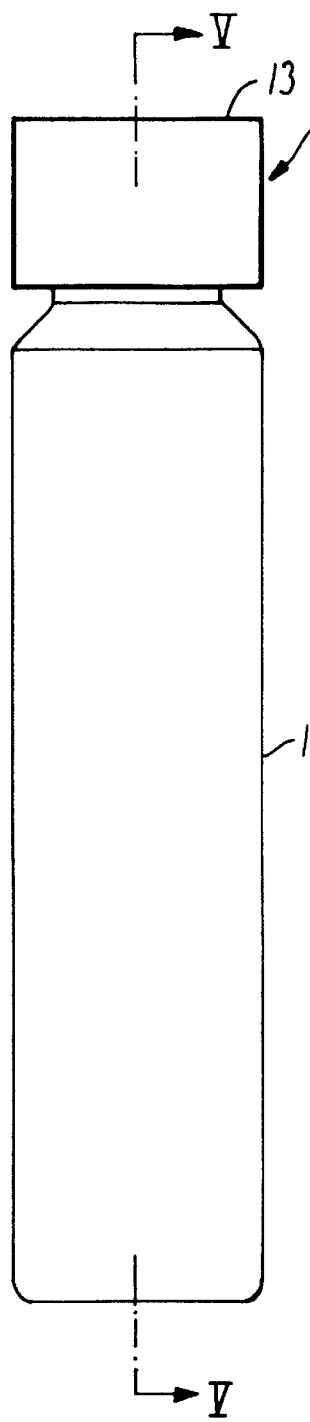
Figure 5:
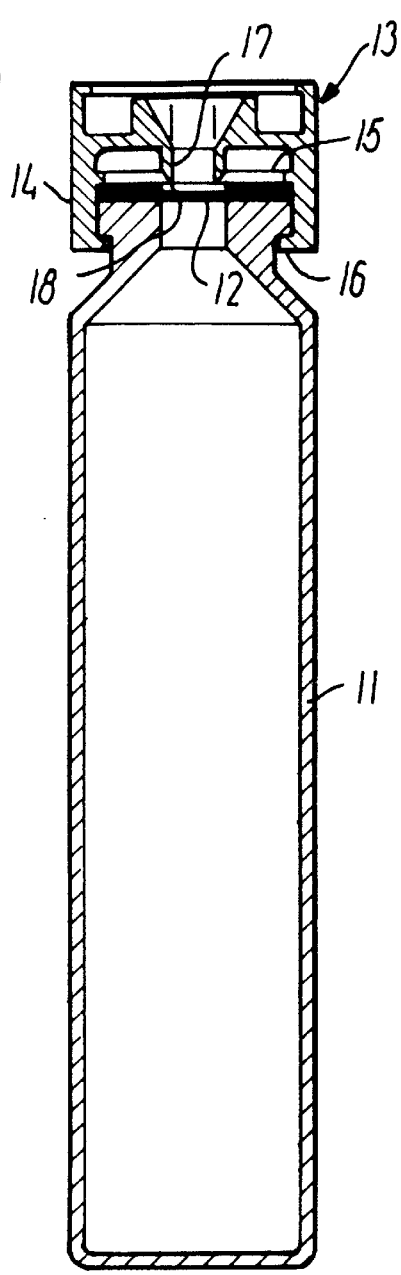
Figure 6:
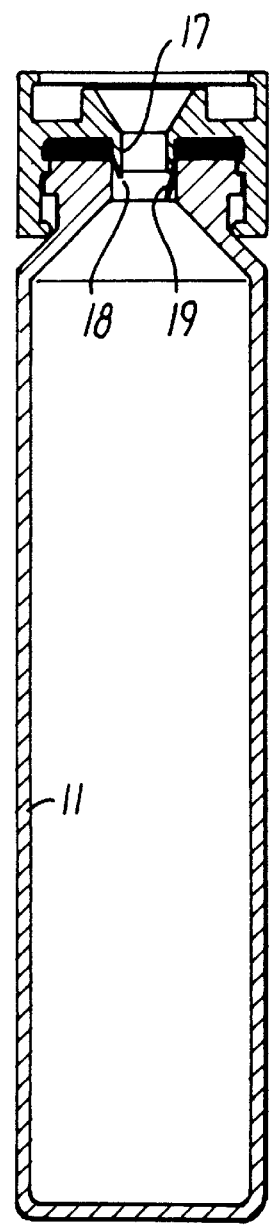
Figure 8:
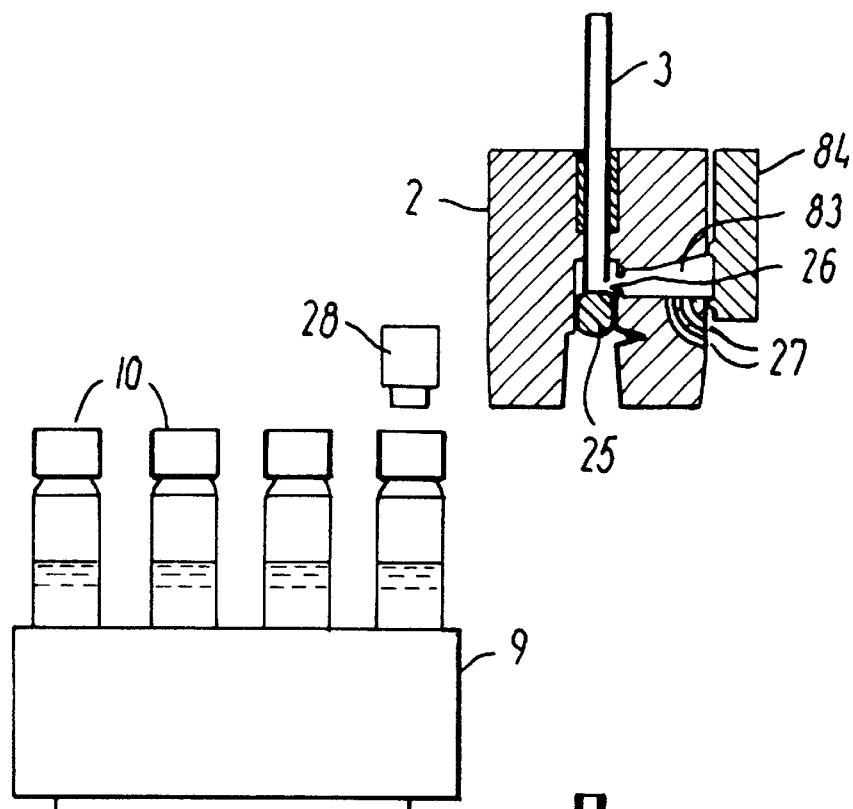
Figure 14:
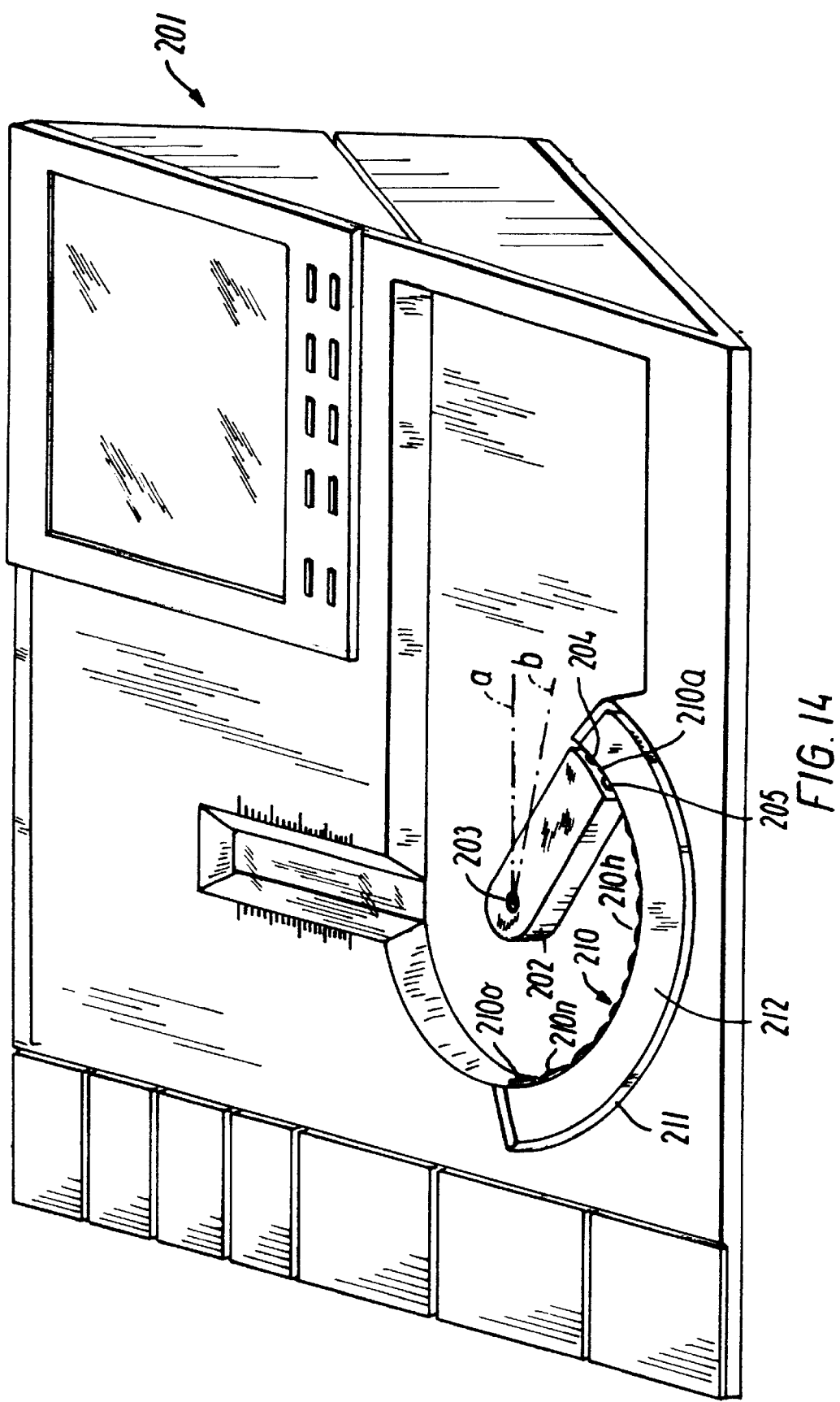
Figure 15:
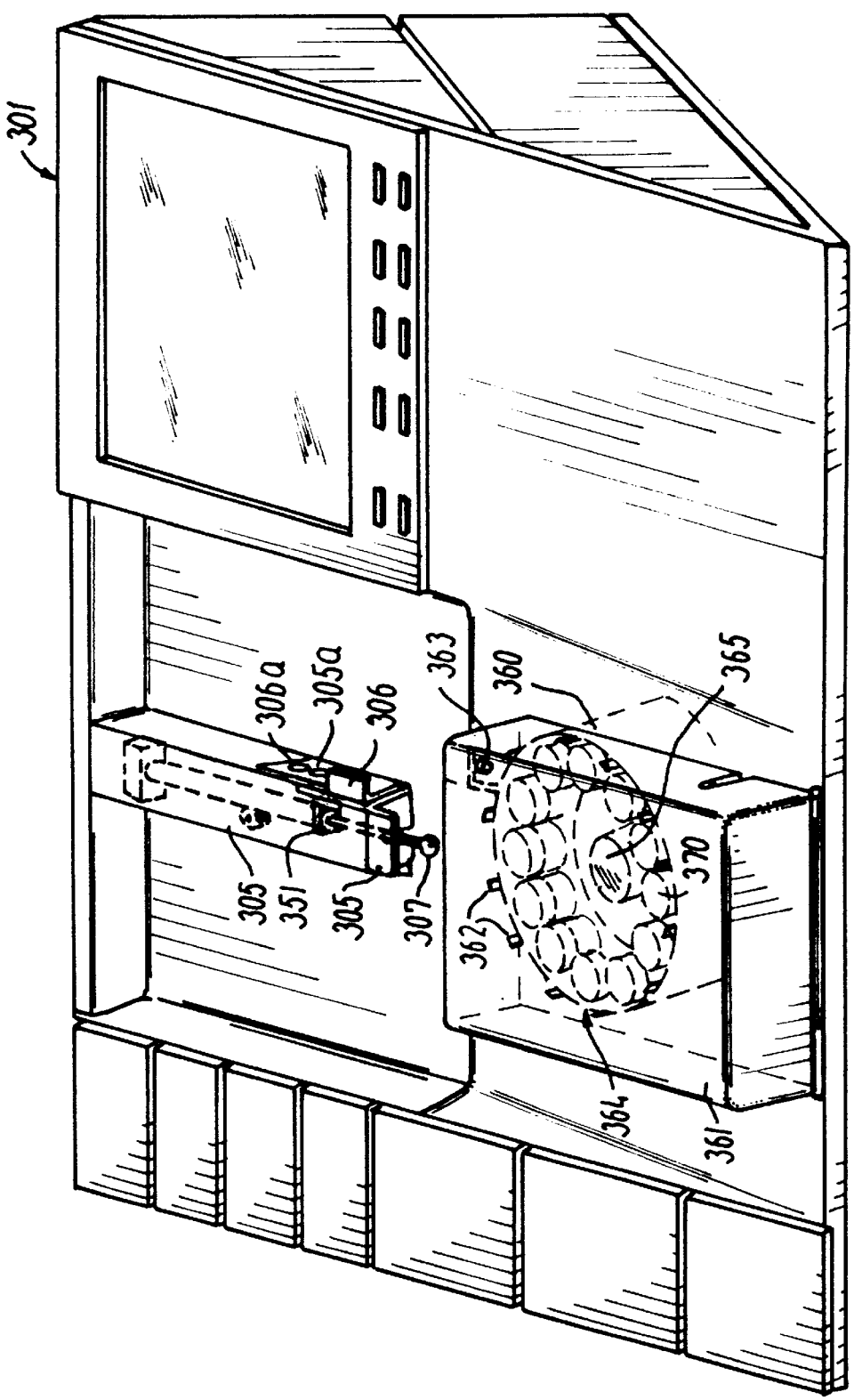
Figure 16:
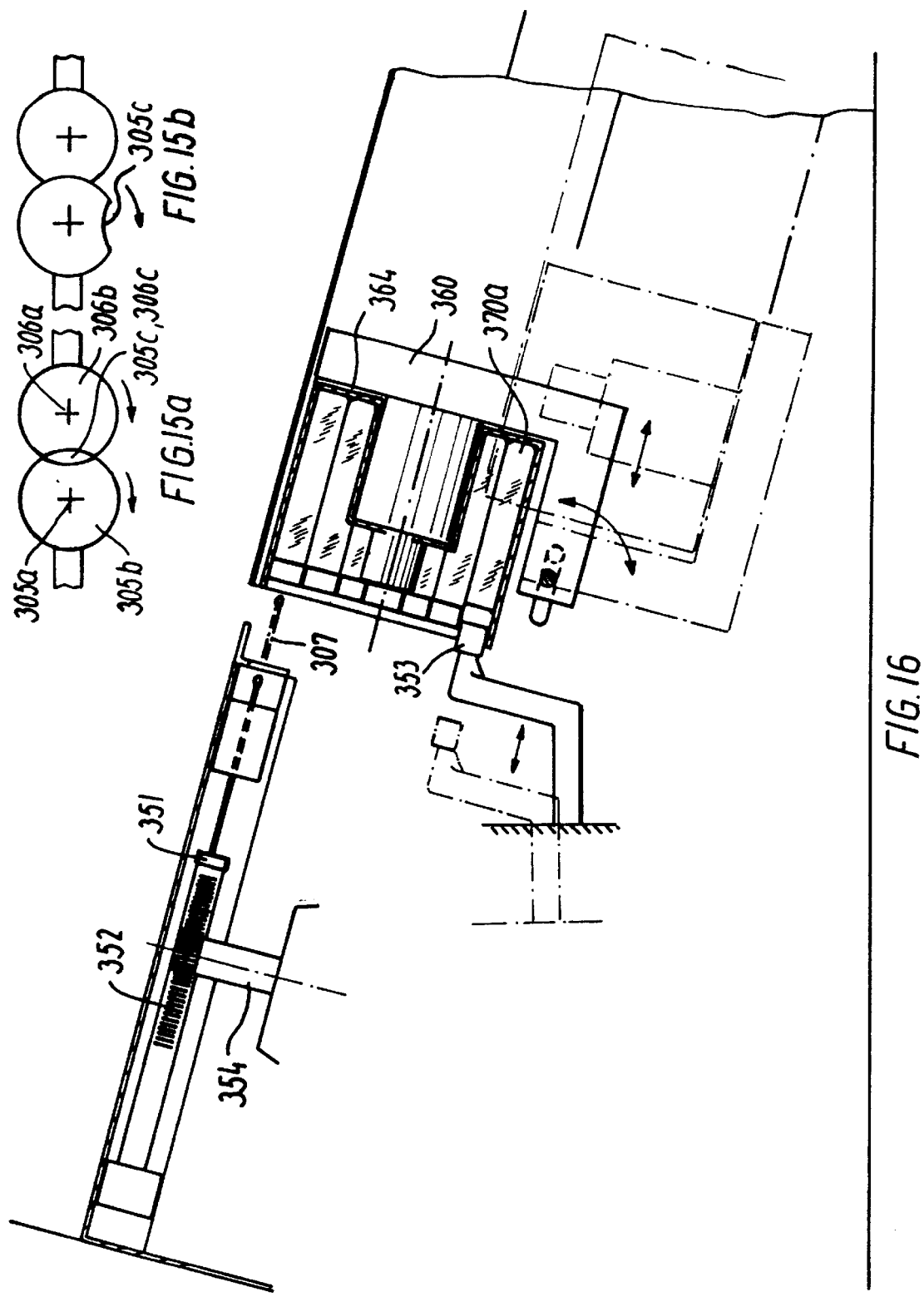
Figure 17:
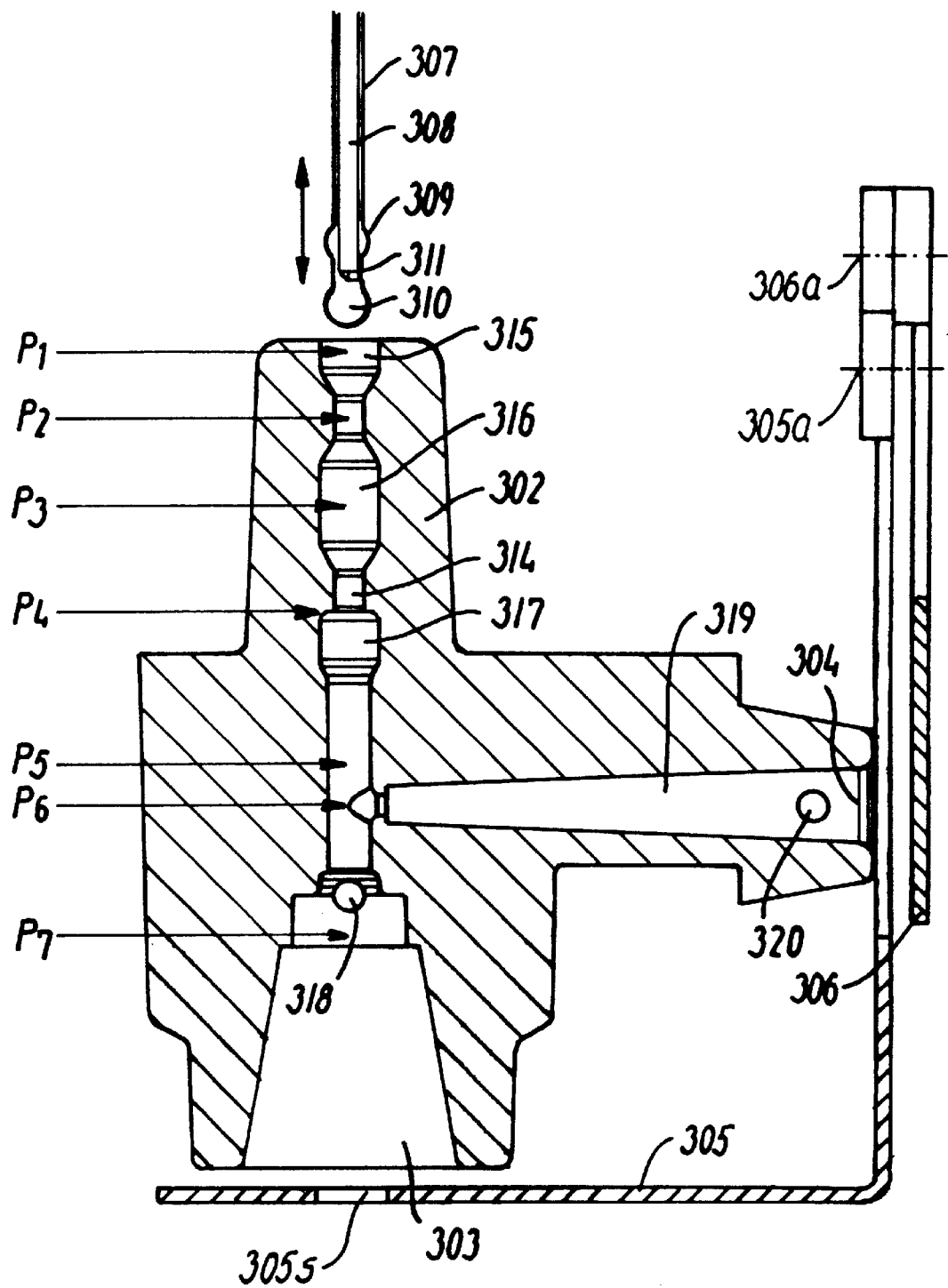
Figure 18:
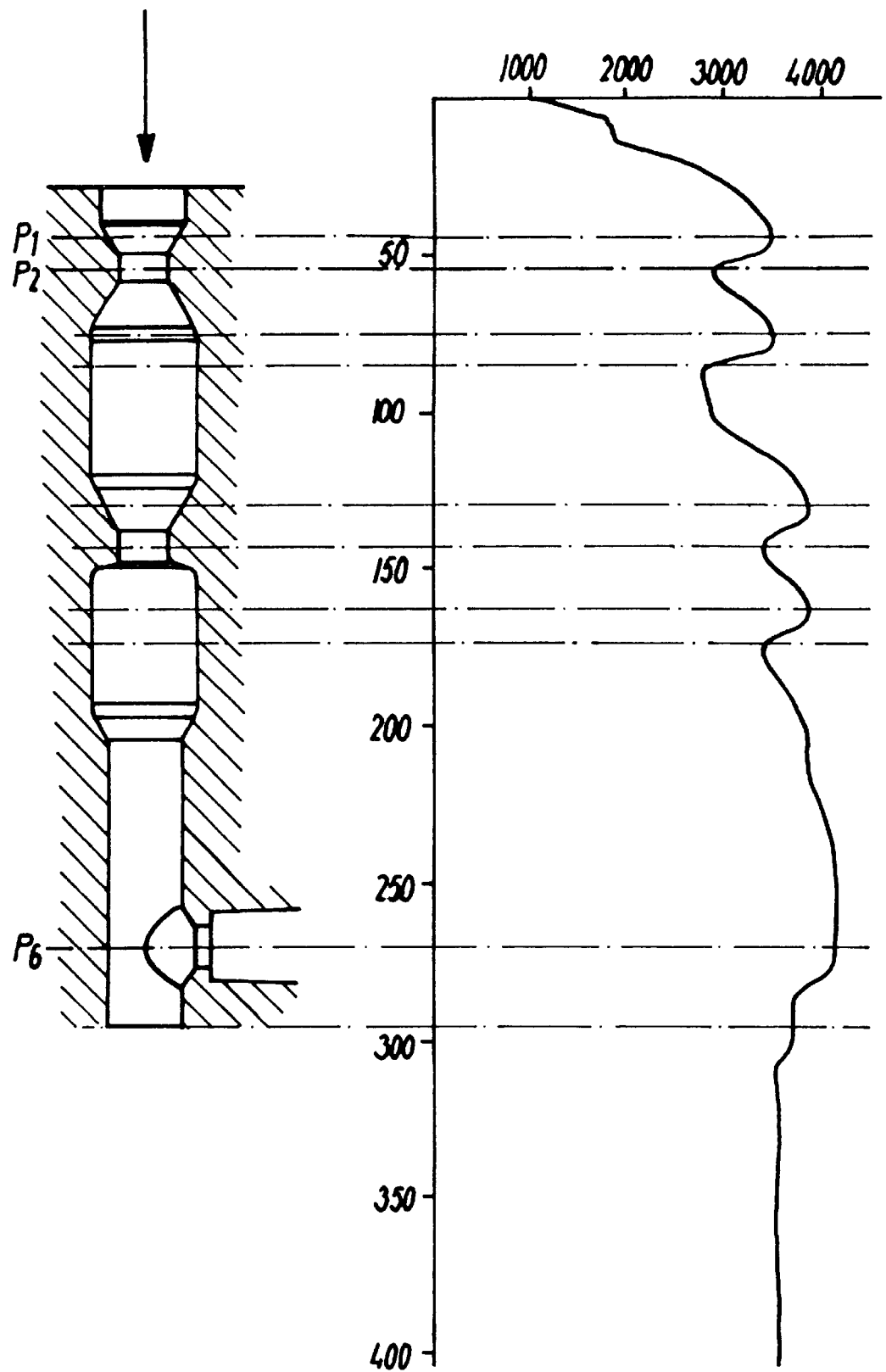

The invention will now be explained in detail by means of examples of embodiments and with reference to the drawing, in which FIG. 1 shows a perspective view of an apparatus for blood gas analysis, FIG. 2 shows a magazine with ampoules, FIG. 3 shows another magazine with ampoules, FIG. 4 shows an ampoule according to the invention with a cap, FIG. 5 shows a sectional view of the ampoule in FIG. 4 along the line V—V, FIG. 6 shows a view corresponding to FIG. 5, but showing the ampoule with the cap pressed down, FIGS. 7a–7c shows different embodiments of details of the ampoule in FIGS. 4–6 shown as a sectional view as FIGS. 5 and 6, FIGS. 8–13 show a sequence of schematical views revealing a device for automatical introduction of control solution and its method of operation, FIG. 14 shows a perspective view of another apparatus for blood gas analysis, FIG. 15 shows a perspective view of yet another apparatus for blood gas analysis FIG. 16 shows a side view of parts of the apparatus of FIG. 15, FIG. 17 shows a schematical view of the inlet gasket of the inlet member of the apparatus of FIGS. 15 and 16, and FIG. 18 shows a curve representing the resistance registered from an inlet tube when the tube is displaced in the inlet gasket shown in FIG. 17.

The apparatus 1 for blood gas analysis as shown in FIG. 1 comprises an inlet member 2 provided with a tube 3 (cf. FIGS. 8–13) through which liquid may be aspirated into the apparatus 1. In FIG. 1 is depicted a blood sample syringe 4, a so-called sampler, inserted in an inlet in the inlet member 2 for analysis of a blood sample in the sampler 4. Furthermore, the inlet member has another inlet 83 for blood samples collected in capillaries. The inlet 83 is also seen in FIGS. 8–13 where it is closed by a flap 84.

The apparatus 1 is shown schematically and besides a built-in PC (personal computer), it comprises a data output display screen/control panel 5, various containers 6 for calibration solutions, cleaning fluids and waste together with a storage room 7 for magazines with quality control solution also called QC solution.

Finally, FIG. 1 shows a unit 82 comprising a holder 81 for a magazine 8 with QC solution and a press element 28 whose function is described below.

The magazine 8 shown in FIG. 1 is better seen in FIG. 2. The magazine comprises a support 9 carrying a number of ampoules 10 containing QC solution. The magazine holder 81 of the apparatus 1 is arranged for displacing the magazine 8 in its longitudinal direction in order to move the ampoules 10 relative to the inlet member 2.

FIG. 3 shows another design of a magazine 8a with a circular support 9a wherein ampoules 10 are placed. The circular support 9a of course requires another holder of the apparatus 1 than the linear support 9 in order to permit a specific ampoule to be moved to the inlet member 2 and the support 9a to be removed completely from the inlet member 2 in order to make room for a sampler 4 as it is shown in FIG. 1.

For the automatic opening of the ampoules by the apparatus 1, a preferred ampoule is shown in FIGS. 4–6. It is to be noted that in connection with the term "ampoule", no allusion is made to a specific shape or material, but merely a small hermetically sealed container. The ampoule shown in FIG. 4 comprises a vial 11 closed at the top by means of a membrane 12 (FIG. 5). Above the membrane 12 is placed a cap 13 which will be described further with reference to FIG. 5.

The cap 13 has a downwardly pending skirt 14 provided with an upper and a lower circumferential bead 15 and 16, respectively, serving to secure the cap on the neck of the vial 11. Furthermore, within the skirt 14, the cap 13 has a tubular penetration part 17, whose lower edge is relatively sharp and descends in a peak 18 which in FIG. 5 is placed just above the membrane 12.

In FIG. 6, the cap 13 has been pressed down whereby the penetration part 17 has pierced the membrane 12 by the peak 18, at first followed by the remaining part of the lower edge of the penetration part 17 such that a loosened lap 19 of the membrane is suspended in the ampoule without being completely detached. At this time, there is access to the contents of the ampoule 10 through the hollow penetration part 17.

FIG. 7a depicts the structure of the membrane 12 and the closing of the ampoule 10. The membrane 12 consists of three layers, namely two co-extruded layers 20 and 21 of polyester with a relatively low and relatively high, respectively, melting point (by way of example 70° C. and 240° C.). Upon the polyester layers 20 and 21 is provided a layer 22 of silicon oxide or aluminum oxide. Above these three layers, there may be provided a protective coating of polymeric material, e.g. polyester, polyethylene or polypropylene for mechanical protection of the layer 22. The thickness of the layers 20, 21, 22 may for example be 3 $\mu$m, 12 $\mu$m and 0.05 $\mu$m, respectively. A possible protective coating of polyethylene or polypropylene may appropriately have a thickness of about 50 $\mu$m. The bottom polyester layer 20 is firmly welded to the mouth of the vial 11 and for a further securing of the impermeability of the vial, a ring 23 of aluminium or alike is crimped on. Between the ring 23 and the membrane 12 is bedded a ring 24 of rubber or similar elastic material which is biased by the crimping of the ring 23.

FIG. 7b is a figure corresponding to FIG. 7a and showing the structure of another embodiment of a membrane 50. The membrane 50 comprises a glass layer which is mounted to the mouth of the ampoule vial by any suitable method. The membrane 50 and the vial 11 may be assembled by means of a glue suitable for adhering to glass and not interacting with or being permeable to any of the components of the reference fluid. Alternatively, the membrane 50 may be welded to the mouth of the vial 11. The welding may be performed in a known manner by melting the glass by means of a gas flame. Another suitable welding method is induction heating whereby a metal string of e.g. wolfram is placed between the membrane and the mouth of the vial 11 and the vial and membrane is placed in an electromagnet.

In a preferred embodiment the glass membrane 50 is laser welded to the vial 11 by means of $CO_2$ laser welding. However, other types of laser welding may be suitable as well, e.g. Nd-YAG laser welding. Laser welding of thin glasses are disclosed e.g. in U.S. Pat. No. 5,489,321.

Further securing of the impermeability of the ampoule 410 is in the embodiment shown provided by rings 23 and 24 as described in connection with the membrane 12 shown in FIG. 7a. Such further securing by rings 23 and 24 is optional as sufficient impermeability may be achieved by the welding itself.

The membrane glass layer 50 preferably comprises a borosilicate glass (the same material as the vial 11) and has a thickness of appx. 80 $\mu$m. Other types of glasses which are capable of sealing the vial without any exchange of matter with the surroundings may be useful as well. Depending on the type of glass the thickness may vary. Thicknesses from 30 $\mu$m to 150 $\mu$m are preferred.

When the means for opening (see FIG. 1) the ampoule is activated to break the membrane 50, small glass particles fall into the ampoule. These glass particles will fall either to the bottom of the ampoule or stay on the surface of the enclosed fluid. Thus, by sucking up the fluid from the middle part of the fluid, no glass particles will be included and entered into the apparatus.

The membrane 50 may be provided with a protective coating of e.g. a polymeric material. When the membrane 50 is broken by the penetration part 17, the protective coating with the broken glass will be suspended in the top of the vial as the membrane 12 described in connection with FIG. 7a. Thus, no small glass particles reach the fluid in the ampoule.

FIG. 7c shows yet another figure corresponding to FIG. 7a and showing the structure of a third embodiment of a membrane 60. The membrane 60 comprises two co-extruded layers 62 and 63 of polyester having a relatively low and relatively high, respectively, melting point (by way of example 70° C. and 240° C.). Upon these layers 62, 63 is a layer 64 of glass e.g. silicon or aluminum oxide. This layer 64 may be applied by either vacuum coating in a thickness of appx. 0.06 $\mu$m or by plasma coating in a thickness of appx. 0.03 $\mu$m. A second layer 66 of glass e.g. silicon or aluminum oxide is in a similar manner applied to a protective coating layer 67 and the two silicon oxide layers 62 and 64 are thereafter assembled by means of a 10–12 $\mu$m layer 65 of a glue suitable for adhering to glass. The protective coating layer 67 is optional and has the same function as the protective coating layer described in connection with the membrane 12 of FIG. 7a.

The bottom layer 62 of the membrane 60 is mounted to the mouth of the ampoule vial 11 by a 10–12 $\mu$m layer 61 of glue suitable for adhering to both glass (the vial 11) and polyester (the layer 62). The membrane 60 is further secured to the mouth of the vial 11 in the same manner as the membrane 12 of FIG. 7a.

It is to be noted that other embodiments of the ampoule 10 than the embodiments described in connection with FIGS. 4–7c may be used in connection with the invention, for example embodiments identical with the embodiments shown in FIGS. 4–7c except that they do not comprise the cap 13 or the rings 23, 24.

FIGS. 8–13 schematically shows the inlet member 2 of the apparatus 1 for blood gas analysis. The inlet member 2 comprises the tube 3 which is displaceable in vertical direction and at its lower end provided with a ball 25 and a suction port 26 placed just above the ball. The inlet member 2 is manufactured from an elastic material so that the ball 25 may bear against the inlet member 2 when the tube 3 is in the position shown in FIG. 8. The inlet member 2 also comprises cleaning fluid channels 27. FIGS. 8–13 further show the vertically movable press element 28 and a magazine 8 with some ampoules 10.

The device shown in FIGS. 8–13 functions in the following way. The inlet member 2 is firstly (FIG. 8) blocked either electronically by the PC of the apparatus or physically by means of a block element. A quality control procedure is initiated either by a user via the control panel of the apparatus or by the PC of the apparatus.

Figure 9:
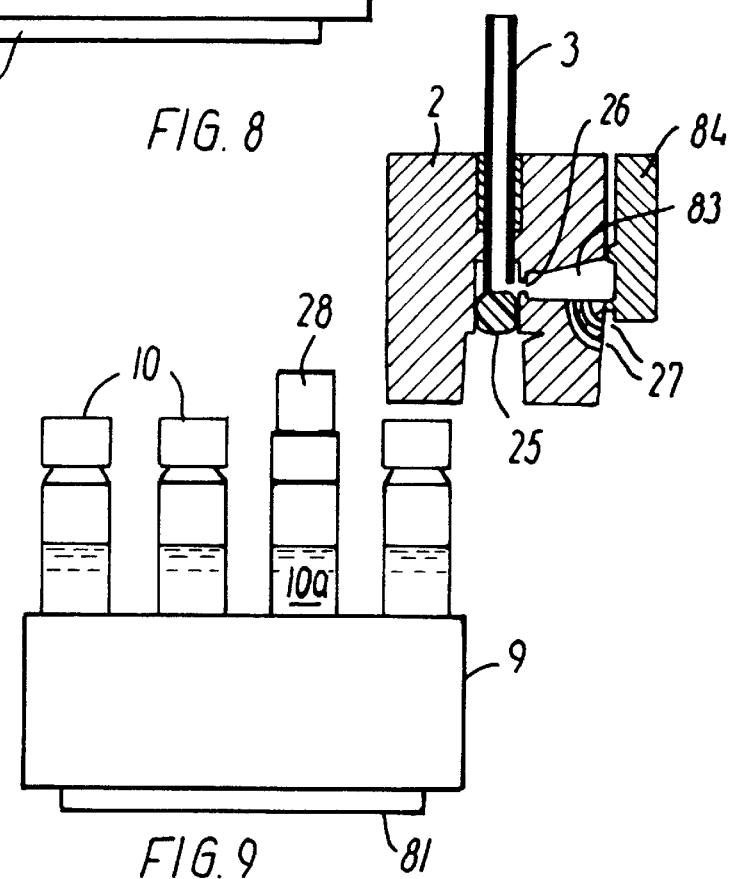

An ampoule with a specific QC solution is chosen by the PC or the user, and the ampoule 10a in question is moved (as the entire magazine 8 is moved) to a position under the press element 28. This element is moved downwards in order to press down the cap 13 of the ampoule 10a such that the membrane 12 is pierced (FIG. 9).

Figure 10:
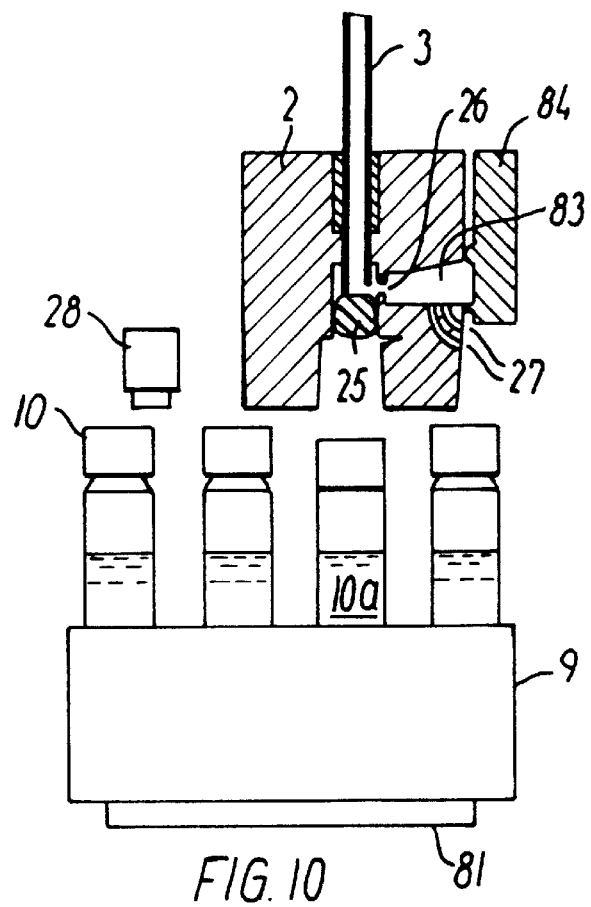
Figure 11:
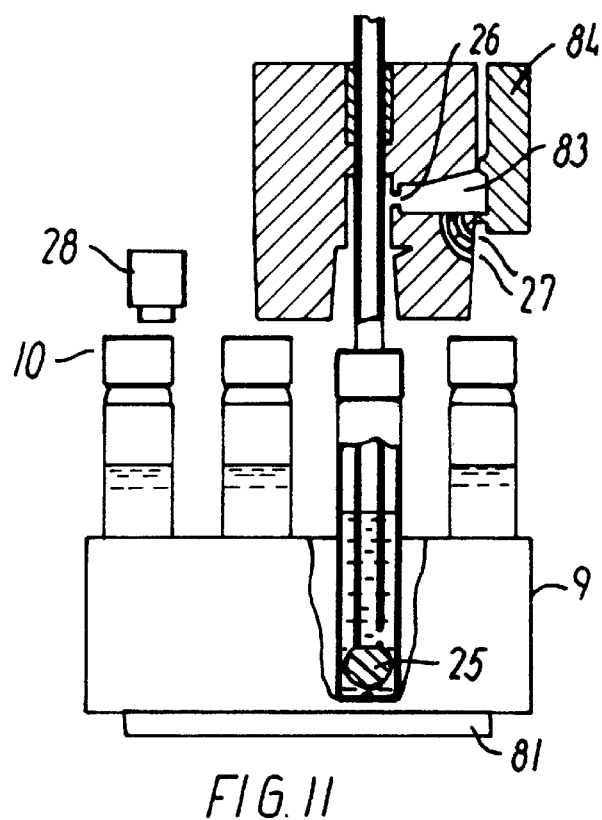
Figure 12:
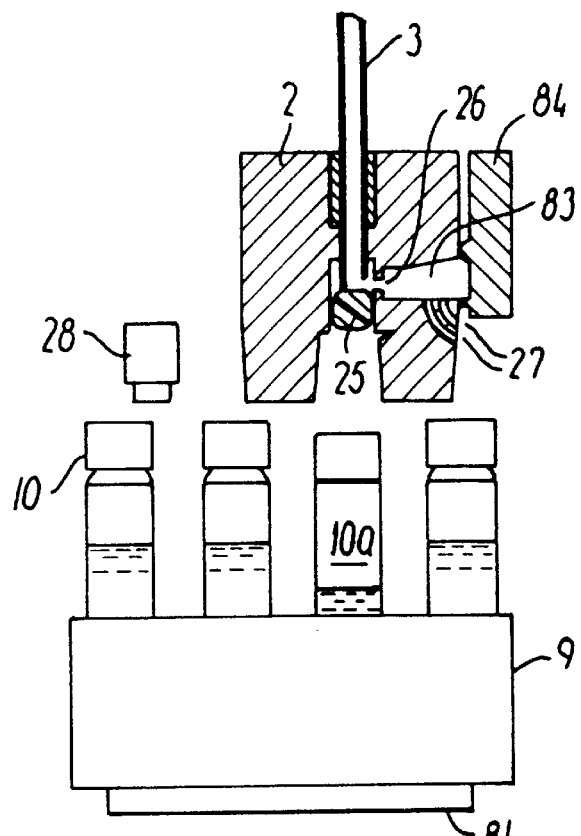
Figure 13:
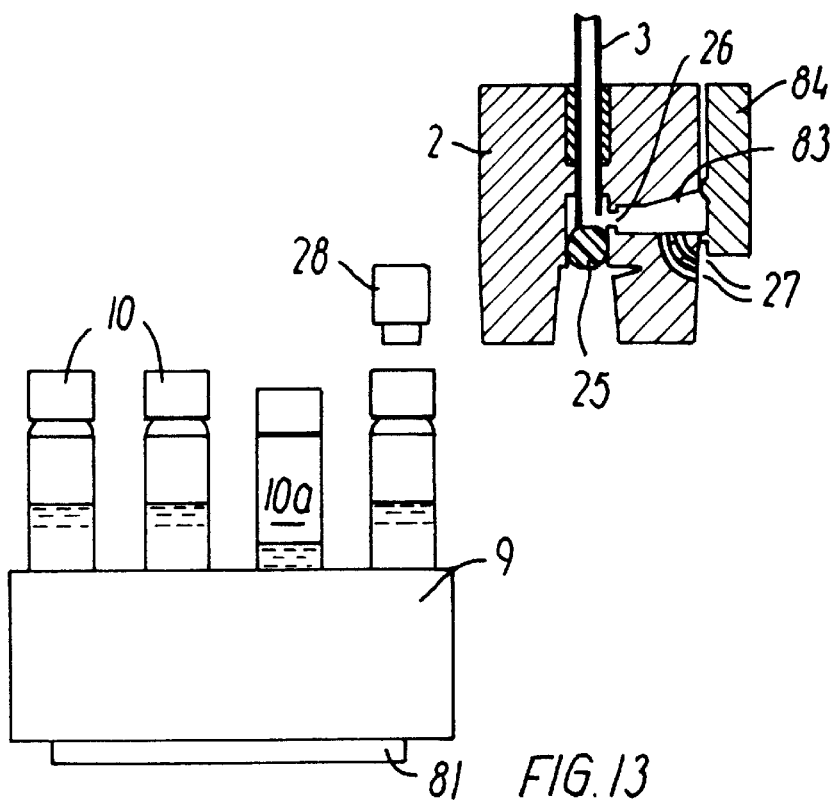

The press element 28 is elevated again and the thus opened ampoule 10a is moved to a position under the tube 3 of the inlet member 2 (FIG. 10). The tube 3 is lowered (FIG. 11) into the ampoule 10a and a predetermined amount of QC solution e.g. 185 µl is aspirated up into the tube. The suction is stopped, the tube is elevated (FIG. 12) and subsequently the suction is resumed such that QC solution aspirated up in the tube is directed to measuring chambers of the apparatus 1 where the quality control is performed in a manner known per se. At this time the magazine 8 with the ampoules 10 is lead back to the initial position from FIG. 8.

When the QC solution is aspirated away from the tube 3, the tube is rinsed by directing cleaning fluid down through the tube 3 and out through the cleaning fluid channels 27. Finally, the cleaning fluid is emptied out of the channels and the apparatus is back to the initial state (FIG. 13) except that an ampoule 10a has been used.

As mentioned above, a quality control of the just described nature should according to guidelines from NCCLS be performed once per shift which means three times a day by treble shift such that in three consecutive shifts, controls are performed with QC solutions containing three different levels for the parameters to be controlled. It is further recommended that by each control, two different levels are measured. Therefore, the QC solution in a given ampoule may for instance have a level distribution with a high value of $pCO_2$, a low value of $pO_2$ and an average pH-value. As to the number of ampoules 10 in a magazine 8, this may for instance be 15 corresponding to a five-day consumption by treble shift. Alternatively, 16 ampoules per magazine may for instance be chosen if QC solutions with four levels for parameter values instead of three are used; thus, a magazine may contain four ampoules times four different level distributions.

As also stated above, it is important that the temperature distribution of the QC solution in an ampoule is uniform and well-known. The uniform distribution may be ensured by shaking an ampoule thoroughly before it is opened, however, alternatively it may be ensured that the ampoules are kept at a known ambient temperature for a longer time. By using magazines 8 containing ampoules 10 in a number sufficient for many days, it is ensured that the ampoules have room temperature. This temperature must then be monitored and it must be ensured that it does not change suddenly. There may, however, be a problem when changing the magazine as by long-time storage, certain QC solutions must be kept in a refrigerator. Therefore, a magazine may advantageously be kept in store in the storage room 7 so that new magazines to be placed in the holder of the apparatus may be taken from the storage room subsequent to a stay for a given minimum time. It is advantageous to monitor the temperature in the storage room 7 with a built-in thermometer whose reading is routinely monitored by the apparatus.

FIG. 14 depicts another design of an apparatus for blood gas analysis. The apparatus 201 shown in FIG. 14 comprises an inlet member 202, through which solution may be aspirated into the apparatus 201. The inlet member 202 is rotatably mounted and may be placed in a number of specific positions (a, b, c, . . . ) when rotating around an axis 203. The inlet member 202 is provided with an inlet 204, through which solution may be aspirated into the apparatus. The inlet member 202 is also provided with a press element 205.

When the inlet member 202 has been placed in position a, it is prepared for insertion of a capillary in the inlet 204. The capillary is then horizontally sited. When the inlet member 202 has been placed in position b, it is prepared for insertion of a sampler in the inlet 204. The sampler will be in a tilted position.

By a further rotation of the inlet member 202, a number of specific positions is passed where either the press element 205 or the inlet 204 has been placed opposite each one of a number of ampoules in an arc-shaped ampoule magazine 212 placed in a holder 211. When the press element 205 is placed opposite a specific ampoule 210a, this ampoule is opened as described in connection with FIG. 1. The inlet member is then rotated clockwise to a neighbouring position where the inlet 204 is placed opposite the ampoule 210a. The suction of the contents in the ampoule is then carried out as described in connection with FIG. 1.

FIG. 15 outlines yet another design of an apparatus for blood gas analysis. The apparatus 301 comprises an inlet member 350 comprising an inlet tube 307 through which solution may be aspirated into the apparatus 301. The inlet tube 307 is mounted in an holder 351 and is displaceable in the inlet member 350.

The inlet member 350 has two separate inlets, one inlet adapted to receive a sample syringe and another inlet adapted to receive a capillary. Each of the inlets is covered by a rotatably mounted inlet flap 305 (syringe inlet) and 306 (capillary inlet) which are interlocked in such a way that the inlet flaps 305, 306 may only be opened one at a time. The flaps 305, 306 do not seal the inlets.

When opening one of the flaps 305, 306, a signal representative of the particular flap 305, 306 is sent to the apparatus indicating the type of inserted sample container, i.e. either a syringe or a capillary. The apparatus is then adjusting the inlet tube 307 for sampling from the relevant container. The flap 305 has a slit 305s through which the tube 307 may pass when collecting fluid from a QC solution ampoule as described below. The slit 305s is so narrow that a syringe may not be inserted in the inlet 303 without opening the flap 305. The inlet member 350 is further described below in connection with FIG. 17.

The apparatus 301 further comprises a holder 360 for holding a magazine 364 of QC solution ampoules 370, the magazine 364 having a circular support 365 as the magazine 8a described in connection with FIG. 3. The centre axis of the holder 360 is inclined appx. 20° to the vertical. The ampoules 370 may be any of the previously described ampoules. The holder 360 is located under a cover 361 which may be removed when changing the magazine 364. The holder 360 is rotatably mounted in the apparatus 301. In order to establish a uniform temperature distribution, the ampoules 370 are centrifuged prior to performing quality control. This is done by rotating the holder 360 with the magazine 364 up to a speed of 400 r/min, stop short, rotate again, stop short etc. When rotating the magazine 364, the QC solution is forced up the walls of the ampoules 370 and falls down when stopping the rotation. By repeating the rotation and stop short a good stirring and thus a uniform temperature distribution of the QC solution is obtained. When inserting a new ampoule magazine 364 a stirring of appx. 30 min. is recommended, whereas prior to performing quality control a stirring of only appx. 5 min. is recommended.

The support 365 of the ampoule magazine 364 has several tabs 362 at the upper rim. The number of tabs 362 equals the number of ampoules 370 less one. The tabs 362 are distributed along the rim of the support 365 uniformly as if there were as many tabs 362 as ampoules 370. Thus, when looking at the support 365 it seems as if one tab is missing. The tabs 362 of the support 365 are sensed by an optical detector 363 of the apparatus 301. Thus, the tabs 362 are used for positioning the ampoules 370 in the holder 360.

The interlocking principle of the inlet flaps 305, 306 is shown in FIGS. 15a–b. Each flap 305, 306 is mounted to rotate around a rotation axis 305a, 306a, respectively. On each flap 305, 306 and in the same plane is placed a circular disk 305b, 306b having radii $R_{305}$ and $R_{306}$, respectively and the centre of which coincides with the respective rotation axis. The disks 305b, 306b are placed with a distance between the axes 305a and 306a less than $R_{305}+R_{306}$. From each disk 305b, 306b is cut away a small part 305c, 306c, corresponding to the "overlapping" part between the disks 305b, 306b. Now, when opening e.g. the flap 305, the disk 305a rotates and "fills out" the cut-away part 306c of disk 306a, thus prohibiting the disk 306a from being rotated and thereby locking the flap 306 (cf. FIG. 15b). Correspondingly, when opening the flap 306 the disk 306a rotates and "fills out" the cut-away part 305c of disk 305a and thus locks the disk 306a and the flap 306.

When a quality control procedure is to be performed at the apparatus 301, the magazine 364 is centrifuged as described above. Depending on the type of quality control an ampoule containing the relevant QC solution is positioned in the position closest to the inlet member 350 by means of the optical detector 363 sensing the position of the tabs 362.

Referring now to FIG. 16, the cover 361 is then lifted and the holder 360 is transferred from the position shown in dotted lines to the position shown in full lines by not shown transferring means. At the same time, a press element 353 of the apparatus 301 is moved towards the holder 360 and the magazine 364. When the holder 360 has reached the position shown, the press element 353 moves against the selected, now lower ampoule 370a and presses down the cap of the ampoule 370a which is then opened. Then the press element 353 is withdrawn and the holder 360 rotated 180° around is centre axis. The selected open ampoule is thus positioned at the top in front of the inlet member 350. The inlet tube 307 may now be displaced through the slit 305s in the flap 305 into the ampoule for aspirating the QC solution into the apparatus 301.

The inlet tube holder 351 is floatingly suspended relatively to a toothed rack 352 which is driven by a motor 354 of the apparatus 301. An analogue Hall-element is placed at the end of the toothed rack 352 and a magnet is mounted on the holder 351. By this system any displacement of the holder 351 relatively to the toothed rack 352 may be detected. The function of this is further described below in connection with FIG. 18.

FIG. 17 is a schematic section of an inlet gasket 302 of the inlet member 350 of the apparatus 301 as seen from above. The inlet gasket 302 is made of Ethylene Propylene Diene Modified rubber (EPDM). Other suitable materials which are sufficiently gastight, elastic and have the appropriate mechanical strength may also be used. The inlet tube 307 of the inlet member 350 is displaceable in its longitudinal direction in a through-going channel 314 of the inlet gasket 302. The tube 307 has an outer diameter of 1,2 mm and an inner channel 308 with a diameter of 0.8 mm. In one end the tube 307 is formed with two external balls 309, 310 each having a diameter of 1.6 mm. The inner channel 308 ends in a suction port 311 having a diameter of 0.45 mm. The suction port 311 is perpendicular to the channel 308 and is located between the balls 309, 310.

The channel 314 in the inlet gasket 302 has different cross-sections along its length, the function of which is further explained below. In one end the channel 314 has an collector 315 for supporting the inlet tube 307 during mounting in the inlet gasket 302. Further along the channel 314 are two chambers 316 and 317. The channel 314 ends in the inlet 303 adapted for the insertion of a syringe. The inlet 303 is formed as a Luer cone. A channel 318 opens into the bottom of the inlet 303. Through this channel 318 a negative pressure may be applied to the inlet 303 for use when draining the inlet 303 from excess sample and rinse solution.

Perpendicular to and opening into the channel 314 is another channel 319 which ends in the inlet 304 adapted for receiving a capillary. The channel 319 is conical which assures safe engagement and tightness with a capillary inserted into the inlet 304 independently of the size of the capillary. In the same manner as the inlet 303, the inlet 304 has a channel 320 for draining excess sample and rinse solution from the inlet 304.

In FIG. 17 several positions P1–P7 are indicated in the inlet gasket 302. These are explained below.

The tube 307 is mounted in the inlet gasket 302 by inserting it into the collector 315. When the suction port 311 reaches the position P1, the ball 310 of the tube 307 bears against the inlet gasket 302 and the tube 307 is guided into the channel 314.

With the tube 307 inserted into the channel 314, the inlet gasket 302 seals against the tube 307 at the position P2 thus preventing fluid in escaping through the collector 315.

When the suction port 311 is located in position P3 the tube 307 is in "ball rinse" position. Rinse fluid guided by the apparatus through the tube 307 may run out through the suction port 311 into the chamber 316 thereby rinsing the balls 309, 310 on the outer surface. The rinse fluid then runs through the channel 314 through the chamber 317 into the inlets 303 and 304 and through the draining channels 318 and 320, respectively.

At position P4 sample residue located at the outer surface of the tube 307 is mechanically scraped off when the tube is withdrawn from a sampling position (see below), i.e. when the tube 307 is moved to the right in the Figure.

When the suction port 311 is located in position P5 both balls 309 and 310 seals against the inlet gasket 302 and the tube 307 is thus sealed.

When the suction port 311 is placed in position P6 the port 311 is in line with the capillary inlet channel 319 while the balls 309 and 310 seal the through-going channel 314 at each side of the channel 319. The tube 307 is now in position for sampling from a capillary inserted into the inlet 304.

At position P7 the suction port 311 is outside the channel 314. In this position the tube 307 may be cleaned by passing air through the inner channel 308.

When the suction port 311 is positioned further out of the inlet gasket 302, the tube 307 is in position for sampling from a syringe inserted in the inlet 303 or from another container located in line with the inlet 303, e.g. a QC solution ampoule, as described above.

In FIG. 18 is shown a curve representing the signal from the Hall-element located at the end of the toothed rack 352 as the inlet tube 307 is displaced in the inlet gasket shown in FIG. 17.

When the inlet tube 307 has been mounted in the holder 351, the tube 307 is displaced all the way through the channel 314 in the inlet gasket 302 and a curve representing the profile of the particular gasket 302 is detected. The curve may thereafter be used to position the inlet tube 307 in the gasket 302. Thus, the mounting of the inlet tube 307 in the holder 351 becomes independent of variations in the inlet gasket 302 as the inlet tube 307 will be positioned relatively to any inlet gasket 302.

Furthermore, it may be detected when the inlet tube 307 touches the bottom of a container, e.g. the piston of a syringe, the bottom of an QC solution ampoule as this will result in a fluctuation in the curve from the Hall-element. By means of this system it may even be detected how far away the particular bottom is from the inlet and it is thus possible to position the inlet tube 307 to aspirate fluid from e.g. the middle of a syringe or ampoule. This is particularly advantageous when using an ampoule with a glass membrane as the ampoule described in connection with FIG. 7b, where small glass particles from a broken membrane 50 are located either on top or at the bottom of the enclosed fluid.

Even though the apparatuses 1, 201, 301 for blood gas analysis so far have been described with automatic quality control, it must be understood that quality control may also be performed manually in the way that an operator chooses an ampoule 10, 210a–o, 370, presses down the cap 13 and places the ampoule in the inlet member 2, 202, 350. The ampoule 10, 210a–o, 370 is thus very suitable for manual use since no sharp edges appear at the opening on which the operator may risk cutting himself as it is the case by the known ampoules with a breakable neck.

Furthermore, it is to be understood that although the invention is primarily described in connection with automatic quality control, it also comprises automatic calibration, the magazine 8, 8a, 212, 364 comprising sealed containers with calibration solution. The term "reference fluid" is used as a common term for control and calibration liquids and gasses.

Besides a specific content of the above stated parameters pH, $pCO_2$ and $PO_2$, the reference fluid may also have a specific content of other parameters, e.g. electrolytes such as $Li^+$, $Na^+$, $K^+$, $Ca^{++}$, $Mg^{++}$, $Cl^-$, $HCO_3^-$ and $NH_{4+}$, hemoglobin, hemoglobin derivates, $TCO_2$, metabolic factors such as bilirubin, glucose, lactate, creatinine, uric acid, pyruvate, ascorbate, phosphate, protein, cholesterol, triglycerides, phenylalanine, tyrosine and urea, and ligands such as antibodies and nucleotide fragments.

What is claimed is:

1. An apparatus for analysis of physiological fluids, with equipment for controlled introduction of reference fluid, the apparatus comprising, measuring means for analyzing sample fluid;

a sample inlet aggregate for introducing sample fluid into the apparatus;

a holder for holding at least one sealed container containing a reference fluid, the sealed container comprising a glass body and a cap with a penetration part adapted to open the sealed container by movement against the body of the sealed container;

a means for selecting from the holder at least one sealed container;

means for opening the sealed container selected by the selecting means, wherein the means for opening the sealed container is separate from the sample inlet aggregate;

means for positioning into a specific position in relation to each other a selected sealed container and the means for opening the selected sealed container;

means for bringing the opened container and the sample inlet aggregate into fluid communication;

means for activating the sample inlet aggregate to introduce reference fluid into the apparatus through the sample inlet aggregate;

means for removing the opened container from fluid communication with the sample inlet aggregate; and programmable control means for control of introduction of reference fluid into the apparatus.

2. An apparatus according to claim 1, wherein the holder is detachable.

3. An apparatus according to claim 1, wherein the holder comprises a device into which the sealed containers may be loaded separately.

4. An apparatus according to claim 1, wherein the holder comprises a support means adapted for removably holding or being attached to a magazine wherein at least one sealed container is held.

5. An apparatus according to claim 1, wherein the means for positioning into the specific position in relation to each other the selected sealed container and the means for opening said sealed container is constituted by the sample inlet aggregate.

6. An apparatus according to claim 1, wherein the means for positioning into the specific position in relation to each other the selected sealed container and the sample inlet aggregate is constituted by the sample inlet aggregate.

7. An apparatus according to claim 5, wherein the sample inlet aggregate is rotatably mounted on the apparatus and the holder is fixedly mounted on the apparatus, and when rotated, the sample inlet aggregate is brought into an introduction position in relation to each of the sealed containers in the holder.

8. An apparatus according to claim 1, wherein the means for positioning into the specific position in relation to each other the selected sealed container and the means for opening said sealed container and/or the sample inlet aggregate comprises means for moving the holder.

9. An apparatus according to claim 1, wherein the means for positioning into the specific position in relation to each other the selected sealed container and the means for opening the sealed container and the means for positioning into the specific position in relation to each other the opened container and the sample inlet aggregate into the specific position in relation to each other are the same.

10. An apparatus according to claim 1, wherein said specific positions of the selected sealed and open container, respectively, is one and the same position.

11. An apparatus according to claim 1, wherein the means for opening the selected sealed container comprises an element which is made to press against an opening area on said sealed container which is thus opened.

12. An apparatus according to claim 1, wherein the sample inlet aggregate comprises a tube arranged for insertion into the opening container.

13. An apparatus according to claim 1, wherein the reference fluid comprises a chemical entity selected from the group consisting of $H^+$, $CO_2$, and $O_2$.

14. An apparatus according to claim 1, wherein the holder has a center axis and a vertical axis, said center axis during the opening of the sealed container and introduction of the reference fluid is inclined at about 20 degrees compared to the vertical axis.

15. An apparatus for analysis according to claim 1, wherein the physiological fluid to be analyzed is blood.

16. An apparatus for analysis according to claim 1, wherein the apparatus is a blood analyzer.

17. An apparatus according to claim 1, wherein the reference fluid is a control solution for quality control of the apparatus and comprises a chemical entity selected from the group consisting of $H^+$, $CO_2$, $O_2$ an electrolyte, hemoglobin, hemoglobin derivatives, $TCO_2$, bilirubin, glucose, lactate, creatinine, uric acid, pyruvate, ascorbate, phosphate, protein, cholesterol, triglycerides, phenylalanine, tyrosine, urea, antibodies, and nucleotide fragments.

18. An apparatus according to claim 17, wherein the electrolyte is selected from the group consisting of $Li^+$, $Na^+$, $K^+$, $Ca^{++}$, $Mg^{++}$, $Cl^-$, $HCO_3^-$, and $NH_4^+$.

19. A unit to be mounted into and to be a part of an apparatus for analysis of blood, the unit being adapted for controlled introduction of reference fluid into the apparatus and comprising:

a holder for holding at least one sealed container containing a reference fluid, the sealed container comprising a glass body and a cap with a penetration part adapted to open the sealed container by movement against the body of the sealed container;

means for opening a sealed container;

means for positioning into a specific position in relation to each other a selected sealed container and the means for opening said sealed container means for bringing the opened container and a sample inlet aggregate of the apparatus into fluid communication, wherein the sample inlet aggregate is separate from the means for opening a sealed container; and means for removing the opened container from fluid communication with the sample inlet aggregate of the apparatus.

20. An unit according to claim 19, wherein the reference fluid is a control solution for quality control of the apparatus and comprises a chemical entity selected from the group consisting of $H^+$, $CO_2$, $O_2$, an electrolyte, hemoglobin, hemoglobin derivatives, $TCO_2$, bilirubin, glucose, lactate, creatinine, uric acid, pyruvate, ascorbate, phosphate, protein, cholesterol, triglycerides, phenylalanine, tyrosine, urea, antibodies, and nucleotide fragments.

21. An unit according to claim 20, wherein the electrolyte is selected from the group consisting of $Li^+$, $Na^+$, $K^+$, $Ca^{++}$, $Mg^{++}$, $Cl^-$, $HCO_3^-$, and $NH_4^+$.

* * * * *